United States Patent
Ahmed et al.

(10) Patent No.: US 10,799,455 B1
(45) Date of Patent: Oct. 13, 2020

(54) MICELLLES CONTAINING ALPHA LIPOIC ACID AS A TRANSDERMAL DRUG DELIVERY SYSTEM

(71) Applicant: King Abdulaziz University, Jeddah (SA)

(72) Inventors: Osama A. A. Ahmed, Jeddah (SA); Khalid M. El-Say, Jeddah (SA); Bader M. Aljaeid, Jeddah (SA); Shaimaa M. Badr-Eldin, Jeddah (SA); Tarek A. Ahmed, Jeddah (SA)

(73) Assignee: King Abdulaziz University, Jeddah (SA)

( * ) Notice: Subject to any disclaimer, the term of this patent is extended or adjusted under 35 U.S.C. 154(b) by 5 days.

(21) Appl. No.: 16/713,878

(22) Filed: Dec. 13, 2019

Related U.S. Application Data

(60) Provisional application No. 62/933,542, filed on Nov. 11, 2019.

(51) Int. Cl.
*A61K 9/107* (2006.01)
*A61K 47/10* (2017.01)
*A61K 47/22* (2006.01)
*A61K 9/00* (2006.01)
*A61K 47/08* (2006.01)
*A61K 9/70* (2006.01)
*A61K 31/4375* (2006.01)

(52) U.S. Cl.
CPC .......... *A61K 9/1075* (2013.01); *A61K 9/0014* (2013.01); *A61K 9/7007* (2013.01); *A61K 31/4375* (2013.01); *A61K 47/08* (2013.01); *A61K 47/10* (2013.01); *A61K 47/22* (2013.01)

(58) Field of Classification Search
CPC .. A61K 9/0014; A61K 9/1075; A61K 9/7007; A61K 31/4375; A61K 47/08; A61K 47/10; A61K 47/22
See application file for complete search history.

(56) References Cited

U.S. PATENT DOCUMENTS

| | | |
|---|---|---|
| 6,193,985 B1 | 2/2001 | Sonne |
| 9,079,874 B2 | 7/2015 | Sugimoto et al. |
| 2004/0024048 A1 | 2/2004 | Wessel et al. |
| 2005/0208082 A1 | 9/2005 | Papas et al. |
| 2013/0345185 A1 | 12/2013 | Mitra et al. |

OTHER PUBLICATIONS

Huang et al., "Technical study of vinpocetine micelles prepared by thin-film hydration method", Zhong Yao Cai. Nov. 2012; 35(11)1850-4.
Moghaddam et al., "Nanoethosomes mediated transdermal delivery of vinpocetine for management of Alzheimer's disease", Drug Delivery, 22:8, 1018-1026 (2015).
Mutalik et al., "Effect of some penetration enhancers on the permeation of glibenclamide and glipizide through mouse skin", Pharmazie Dec. 2003; 58(12):891-4.
Nishiura et al., "A novel nano-capsule of alpha-lipoic acid as a template of core-shell structure constructed by self-assembly", J Nanomed Nanotecnol 2013, 4:1.
Yang et al., "Recent advances in the application of vitamin E TPGS for drug delivery", Theranostics 2018, vol. 8, Issue 2: 464-485.

*Primary Examiner* — Barbara P Badio
(74) *Attorney, Agent, or Firm* — W & C IP

(57) ABSTRACT

Micelle formulations comprising a tocopherol or derivative thereof, alpha lipoic acid, and a biologically active agent such as vinpocetine are provided. Films for transdermal delivery containing the micelle formulation and methods of treating cognitive and cerebrovascular disorders are also provided.

7 Claims, 5 Drawing Sheets

MICELLLES CONTAINING ALPHA LIPOIC ACID AS A TRANSDERMAL DRUG DELIVERY SYSTEM

CROSS-REFERENCE TO RELATED APPLICATIONS

This application claims the benefit of U.S. Provisional Application 62/933,542 filed Nov. 11, 2019, the complete contents of which are incorporated herein by reference.

FIELD OF THE INVENTION

The invention is generally related to micelles containing alpha lipoic acid for the transdermal delivery of biological active agents such as vinpocetine to treat cognitive and cerebrovascular disorders.

BACKGROUND OF THE INVENTION

Drug solubility has been a common limitation in the development of new drug formulations. This may not be surprising given that more than a third of the drugs listed in the United States Pharmacopoeia are either poorly soluble or insoluble in water. Additionally, it is well known that for many drugs the rate-limiting step for the absorption within the gastrointestinal tract, is its dissolution. Thus, new formulations are needed to enhance the dissolution rate of poorly soluble drugs and increase their bioavailability.

Vinpocetine (VNP), derived from the natural vinca alkaloid vincamine, is widely utilized as a vasodilator and a nootropic agent.[1,2] VNP is used for improving memory and cerebral metabolism in cerebrovascular and age-related memory disorders.[3,4] The extensive first pass drug metabolism and low aqueous solubility hinders the full utilization of VNP oral dose because of its low oral bioavailability.[5]

Due to the bioavailability problems with oral delivery of VNP, alternative and effective formulations for VNP delivery are needed.

SUMMARY OF THE INVENTION

An aspect of the disclosure provides a micelle formulation, comprising a tocopherol or derivative thereof; alpha lipoic acid (ALA); and VNP. In some embodiments, the tocopherol is D-α-Tocopherol polyethylene glycol 1000 succinate (TPGS).

Another aspect of the disclosure provides a film for transdermal drug delivery comprising micelles according to the disclosure and further comprising citral and propylene glycol. In some embodiments, the percentage of ALA in tocopherol is 1-30%, the citral concentration is 1-3%, and the propylene glycol concentration is 1-5%. In some embodiments, the percentage of ALA in tocopherol is 16.62%, the citral concentration is 3%, and the propylene glycol concentration is 2.18%.

Another aspect of the disclosure provides a method of enhancing cognition and/or memory in a subject in need thereof, comprising topically applying a film according to the disclosure to the subject.

Another aspect of the disclosure provides a method of treating a cognitive disorder in a subject in need thereof, comprising topically applying a film according to the disclosure to the subject. In some embodiments, the cognitive disorder is selected from the group consisting of dementia, Huntington's disease, Parkinson's disease, and Alzheimer's disease.

Another aspect of the disclosure provides a method of treating a cerebrovascular disorder in a subject in need thereof, comprising topically applying a film according to the disclosure to the subject. In some embodiments, the cerebrovascular disorder is selected from the group consisting of stroke, vertebral stenosis, intracranial stenosis, aneurysm, and a vascular malformation.

DETAILED DESCRIPTION

Figure 1A:
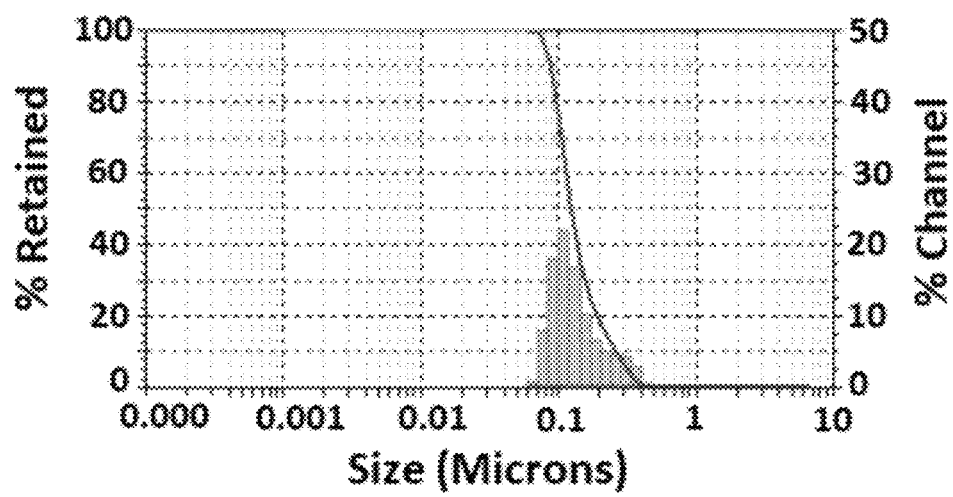
FIG. 1A-B. Particle size distribution measured by particle size analyzer (A) and TEM photomicrographs (B) of VNP-TPGS-ALA micelles.

Embodiments of the disclosure provide tocopherol and ALA containing micelles useful for the transdermal delivery of biological active agents such as VNP. The nanostructured-based transdermal film system according to embodiments of the disclosure improves the diffusion of active agents and is thus useful for improving treatment effectiveness of the delivered therapeutic agents.

As used herein, the term "micelle" refers to an aggregate (or cluster) of surfactant molecules. Micelles only form when the concentration of surfactant is greater than the critical micelle concentration (CMC). Surfactants are chemicals that are amphipathic, which means that they contain both hydrophobic and hydrophilic groups. Micelles can exist in different shapes, including spherical, cylindrical, and discoidal. A micelle comprising at least two different molecular species is a mixed micelle.

Polymeric micelles are exploited as pharmaceutical nanocarriers for the delivery of poorly water-soluble (i.e., water-insoluble) or hydrophobic drugs, which can be solubilized in the hydrophobic inner core of a micelle. Micelles can therefore serve to improve solubility and bioavailability of various hydrophobic drugs. The small size of micelles (typically about 10 to about 100 nm) allows for efficient accumulation of an associated active moiety into targeted tissues. Micelles can be formed from one or more polymeric nonionic surfactants.

Embodiments of the disclosure provide a tocopherol or derivative thereof as a nonionic surfactant. Tocopherols are a class of methylated phenols, many of which have vitamin E activity. Tocopherols and their derivatives, such as esters for example, are widely used in vitamin supplementation and as antioxidants in the food industry and in many pharmaceutical compositions. Tocopherols are a range of natural and synthetic compounds, also known by the generic term Vitamin E α-Tocopherol (chemical name: 2,5,7,8-tetramethyl-2-(4',8',12'-trimethyldecyl)-6-chromanole) is the most active and widely distributed in nature, and has been the most widely studied. Other members of the class include beta, gamma, and delta tocopherols. Tocopherols occur in a number of isomeric forms, the D and DL forms being the most widely available. As used herein, the term "tocopherol" includes all such natural and synthetic tocopherol or Vitamin E compounds.

Any of the forms or isomers of tocopherols and their derivatives, eg. esters may be used according to the present disclosure. Thus for example, α-tocopherol can be used as such or in the form of its esters such as α-tocopherol acetate, linoleate, nicotinate or hemi succinate-ester, many of which are available commercially.

The tocopherol derivative includes chemical derivatives of vitamin E with ester and ether linkages of various chemical moieties to polyethylene glycol of various lengths. For example, the derivative may include vitamin E tocopherol polyethylene glycol succinate (TPGS) derivatives with PEG molecular weights between about 500 and 6000 Da. In some embodiments, the vitamin E polymeric derivative is D-α-Tocopherol polyethylene glycol 1000 succinate (TPGS). In an embodiment, the TPGS is present in the composition from about 0.01 wt % to about 20 wt %/volume. It should be understood that throughout the specification the term weight percent (wt %) refers to mass per unit volume, unless otherwise specified.

TPGS is a water soluble derivative of Vitamin E in which polyethylene glycol subunits are attached by a succinic acid diester at the ring hydroxyl of the vitamin E molecule. TPGS is an almost odourless waxy amphiphilic substance with a molecular weight about 1513. TPGS forms stable micelles in aqueous vehicles for its amphiphilic structure with a hydrophile/lipophile balance (HLB) value of 13.2. TPGS has been approved as a pharmaceutical excipient by the United States Food and Drug Administration (FDA).[11]

The tocopherol surfactant of the disclosure may be used alone or in conjunction with other known surfactants eg. phospholipids, polysorbates, sorbitan esters of fatty acids, cetearyl glucoside or poloxamers or other stabilisers such as xanthan gum, or propylene glycol alginate. Preferably, the total amount of surfactants in the compositions of the presently disclosed embodiments is about 30 percent or less of the total composition with the remaining major component being water.

The micelle compositions of the disclosure also include α-Lipoic acid (ALA), also known as thioctic acid. ALA is a substance in the form of yellow crystals having the structural formula $C_8H_{14}O_2S_2$ and the molecular weight of 206.3. ALA is also present in the human body, and is contained in many foods such as broccoli and red meat. ALA is an antioxidant that protects membranes through recycling vitamin E.[16] ALA can function as a redox regulator and showed effects in various oxidative stress models as ischemia-reperfusion injury and diabetes.[17-20] In addition to its use as an oxidative agent, ALA being included in the micelle compositions of the disclosure also provides for enhancement of cognitive functioning in patients. In some embodiments, the percentage of ALA in TPGS in the micelle compositions disclosed herein is 1-30%, e.g. 10-20%, e.g. about 16.62%.

The present disclosure provides the use of a tocopherol or a derivative thereof in combination with ALA for the preparation of a micelle composition for delivery of a substantially insoluble or sparingly soluble biologically active agent to a human or non-human animal subject. In some embodiments, the active agent has a solubility in water (w/v) which is 3% or less, e.g. 1% or less. In some embodiments, the active agent is VNP. In some embodiments, the active agent is an apovincaminic acid derivative. In some embodiments, the active agent is a PDE1 inhibitor. In some embodiments, the amount of active agent incorporated into the micelle composition is 5-50 mg.

The present disclosure also provides a method of treatment of a human or non-human animal subject by delivery of a substantially insoluble or sparingly soluble biologically active agent, said method comprising administering to said subject a micelle composition of the invention as hereinbefore defined.

The compositions of the present disclosure may also contain other components such as, but not limited to, additives, adjuvants, buffers, tonicity agents, bioadhesive polymers, and preservatives. In any of the compositions of this disclosure, the mixtures are preferably formulated at about pH 5 to about pH 8. This pH range may be achieved by the addition of buffers to the composition. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values. The micellar compositions of the present disclosure are stable in buffered aqueous solution. That is, there is no adverse interaction between the buffer and any other component that would cause the compositions to be unstable.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight.

In an embodiment, a composition of the present disclosure includes at least one bioadhesive polymer. Bioadhesive polymers of the present disclosure include, for example, carboxylic polymers like CARBOPOL® (carbomers), NOVEON (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, polyvinyl pyrollidone, polyethylene glycol, PLURONIC® (Poloxamers), tragacanth, and hyaluronic acid; phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil.

In an embodiment, if a preservative is desired, the compositions may optionally be preserved with any well-known system such as benzyl alcohol with/without EDTA, benzalkonium chloride, chlorhexidine, COSMOCIL® CQ (a preservative), or DOWICIL 200 (a preservative).

The compositions disclosed herein have the bioactive agent, e.g. VNP, incorporated and/or encapsulated in micelles which are dispersed in an aqueous medium or formed into a dosage form suitable for transdermal absorption.

Examples of the dosage forms for transdermal absorption into the skin include ointments, thickening gel systems, lotions, water in oil emulsions, oil in water emulsions, solids, sheets, films, powders, gels, mousse and sprays. The external preparation for skin may be a sheet or fabric impregnated with the preparation. Methods for preparing such dosage forms are known in the art.

The dosage form of the disclosure, such as a film, may also include skin penetration enhancers (also called sorption promoters or accelerants) which penetrate into skin to reversibly decrease the barrier resistance. Examples include, but are not limited to, sulphoxides (such as dimethylsulphoxide, DMSO), Azones (e.g. laurocapram), pyrrolidones (for example 2-pyrrolidone, 2P), alcohols and alkanols (ethanol, or decanol), glycols (for example propylene glycol, PG), surfactants and terpenes (e.g. citral). In some embodiments, the dosage form includes propylene glycol and citral (e.g. available from Sigma-Aldrich (CAT #: C83007) 3,7-Dimethyl-2,6-octadienal, Geranial and neral mixture). In some embodiments, the propylene glycol concentration is 1-5%, e.g. 2-4%, e.g. 2.18%. In some embodiments, the citral concentration is 1-5%, e.g. 1-3%, e.g. 3%.

Embodiments of the disclosure also include methods of preparing the micelle compositions disclosed herein. Various suitable methods are known in the art. In an embodiment, the present disclosure provides a method of preparing a mixed micelle composition that includes mixing an active agent (e.g. VNP) with a tocopherol (e.g. TPGS) and ALA in ethanol to form an ethanolic solution. In an embodiment, the method provides for adding distilled water to the prepared solution. The ethanol may then be evaporated, e.g. using a rotary vacuum evaporator. The prepared dispersion may then be centrifuged and the residue lyophilized using a freeze dryer.

Other suitable solvents that can be used in preparing the micelle compositions of the present disclosure include short-chain alcohols, for example, methanol, n-propanol, isopropanol, and butanol, as well as, chloroform, acetone, methylene chloride, dimethyl dulfoxide, dimethyl formamide and propylene glycol.

Embodiments of the disclosure also provide methods of preparing transdermal films. In an embodiments, the prepared micelles are dispersed in distilled water. Skin penetration enhancers and other additives such as hydroxypropyl methylcellulose, citral, and propylene glycol may then be added. The preparation may then be poured onto a contained surface, e.g. a petri dish, to allow for complete evaporation of water and formation of the film. The film may be incorporated into known transdermal delivery devices, e.g. in a patch containing an adhesive for application to the skin.

The compositions and dosage forms of the disclosure may be useful for the treatment of any disease or disorder that the included active agent is useful for treating. For example, in VNP is used, the composition or dosage form may be useful for the treatment of cerebrovascular disorders such as stroke, vertebral stenosis, intracranial stenosis, aneurysm, and a vascular malformation and cognitive disorders such as dementia, Huntington's disease, Parkinson's disease, and Alzheimer's disease. In some embodiments, the composition or dosage form may be used to enhance cognition and/or memory in a healthy subject not having a cerebrovascular or cognitive disorder. In some embodiments, the composition or dosage form is used for the treatment of circulatory disorders which may occur in smokers and diabetics.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. VNP) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In an embodiment, the composition or dosage form of the disclosure is applied topically to any body surface, including the skin and all other epithelial or serosal surfaces. However, whilst the beneficial effects of the disclosure are particularly apparent in transdermal delivery, the utility of the disclosure is not limited and micelle compositions according to the invention may also be administered parenterally or enterally, eg. as implants or by intravenous, intramuscular or subcutaneous injection, by infusion, or orally.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

This work aimed at utilizing D-α-Tocopherol polyethylene glycol 1000 succinate (TPGS) and alpha lipoic acid (ALA) to develop efficient micellar system for transdermal delivery of VNP. VNP-TPGS-ALA micelles were prepared, characterized for particle size using particle size analyzer and investigated for structure using transmission electron microscope. Optimization of VNP-TPGS-ALA micelles loaded transdermal films was performed using Box Behnken experimental design. The investigated factors were percentage of ALA in TPGS ($X_1$), citral concentration ($X_2$) and propylene glycol concentration ($X_3$). Elongation percent ($Y_1$), initial permeation after 2 h ($Y_2$) and cumulative permeation after 24 h ($Y_3$) were studied as responses. Statistical analysis revealed optimum levels of 16.62%, 3%, and 2.18% for $X_1$, $X_2$, and $X_3$, respectively. Fluorescent laser microscopic visualization of skin penetration for the optimized transdermal film revealed marked widespread fluorescence intensity in skin tissue after 0.5, 2 and 4 h compared with raw VNP transdermal film formulation that indicated enhancement of VNP skin penetration. The obtained results highlighted the use of VNP nanostructured-based films for controlling the transdermal permeation of the drug and improving its effectiveness.

Materials and Methods

Materials

VNP, TPGS, citral, propylene glycol (PG), ethanol, hydroxypropyl methylcellulose viscosity 4000 centipoise (2% w/v solution) and fluorescein isothiocyanate-dextran (FITC-dextran) (average Molecular Weight 20,000) were purchased from Sigma-Aldrich (St. Louis, Mo., USA).

Preparation of VNP-TPGS-ALA Micelles

VNP loaded TPGS-ALA micelles were prepared by dissolving VNP, TPGS and ALA in ethanol using magnetic stirrer for 5 minutes.[27] Distilled water was then added to the prepared solution. After dispersion of the components, ethanol was removed using rotary evaporator (BUCHI Labortechnik AG, Flawil, Switzerland). The prepared dispersion was then centrifuged at 30,000 rpm for 45 min at 4° C. The residue was lyophilized using freeze dryer (alpha 1-2 LD plus, Christ lyophilizer, Germany) for 48 h and stored for further characterization study.

Evaluation of VNP-TPGS-ALA Micelles

Particle size: The prepared VNP-TPGS-ALA dispersion was investigated for mean particle size by light scattering technique using Zetatrac particle size analyzer (Microtrac Inc., PA, USA).[28]

Transmission electron microscope: A sample of VNP-TPGS-ALA micelles preparation was exposed to transmission electron microscope (TEM) (100CX, JEOL, Tokyo, Japan). A drop of diluted micelles was added onto a TEM grid and then stained with 2% uranyl acid. The grid was dried before investigation.[29]

Box-Behnken Experimental Design for VNP-TPGS-ALA Transdermal Films Based on preliminary investigation of VNP-TPGS-ALA transdermal formulations, three factors three level Box-Behnken experimental design (Statgraphics Centurion XV version 15.2.05 software, StatPoint Technologies Inc., Warrenton, Va., USA) was used to investigate the effect of the studied variables.[30] A total of 15 runs was constructed with fully randomized order of experiments. The investigated independent variables (factors) were percentage of ALA in TPGS ($X_1$), citral concentration ($X_2$) and PG concentration ($X_3$). The studied dependent variables (responses) were elongation percent ($Y_1$), initial permeation after 2 h ($Y_2$) and cumulative permeation after 24 h ($Y_3$) of the prepared VNP-TPGS-ALA films. The levels of the investigated independent variables and the constraints for the dependent variables are shown in Table 1. The design was constructed to maximize the elongation percent and to achieve sustained permeation profile of drug from the transdermal films with VNP initial permeation of 20% after 2 h and cumulative permeation of 75% after 24 h.

TABLE 1

Independent and dependent variables of VNP-TPGS-ALA transdermal film formulations in Box-Behnken design.

| Independent Variables | Unit | Levels | | |
|---|---|---|---|---|
| | | −1 | 0 | 1 |
| ALA in TPGS (X1) | % | 0 | 15 | 30 |
| Citral concentration (X2) | % | 1 | 2 | 3 |
| PG concentration (X3) | % | 1 | 3 | 5 |

| Dependent variables | Unit | Constraints | | |
|---|---|---|---|---|
| | | Low | High | Goal |
| Elongation (Y1) | % | 5 | 140 | 72.5 |
| Initial permeation after 2 h (Y2) | % | 10.24 | 30.36 | 20.3 |
| Cumulative permeation after 24 h (Y3) | % | 57.72 | 97.29 | 77.5 |

Abbreviations:
VNP; Vinpocetine, ALA; alpha lipoic acid, TPGS; D-a-Tocopherol polyethylene glycol 1000 succinate, PG; propylene glycol concentration.

Preparation of VNP-TPGS-ALA Transdermal Films

According to the formulation composition depicted in the experimental design (Table 2), VNP-TPGS-ALA transdermal films were prepared by the dispersion of the prepared micelles containing VNP equivalent to 40 mg in 50 mL distilled water. Hydroxypropyl methylcellulose (2% w/v) and specified amounts of the penetration enhancer (citral) and propylene glycol (PG), as plasticizer, were added.[31] The dispersion was stirred using magnetic 1E) stirrer and then kept for 24 h in the fridge. After that, the preparation was poured in glass petri dish (9 cm diameter) and stored at 40° C. until complete evaporation of water and formation of the films.

TABLE 2

Composition of VNP-TPGS-ALA transdermal film formulations and their observed responses.

| run | X1 (%) | X2 (%) | X3 (%) | Y1 (%) | Y2 (%) | Y3 (%) |
|---|---|---|---|---|---|---|
| 1 | 15.0 | 1.0 | 5.0 | 125.0 | 20.89 | 71.85 |
| 2 | 0.0 | 2.0 | 5.0 | 130.0 | 22.3 | 92.15 |
| 3 | 15.0 | 1.0 | 1.0 | 25.0 | 14.86 | 66.43 |
| 4 | 15.0 | 3.0 | 1.0 | 5.0 | 19.67 | 73.1 |
| 5 | 15.0 | 2.0 | 3.0 | 95.0 | 17.9 | 80.89 |
| 6 | 30.0 | 2.0 | 1.0 | 20.0 | 11.84 | 64.41 |
| 7 | 15.0 | 2.0 | 3.0 | 90.0 | 17.72 | 78.96 |
| 8 | 0.0 | 1.0 | 3.0 | 85.0 | 21.58 | 86.65 |
| 9 | 15.0 | 3.0 | 5.0 | 140.0 | 18.44 | 89.66 |
| 10 | 0.0 | 3.0 | 3.0 | 110.0 | 30.36 | 97.29 |
| 11 | 30.0 | 1.0 | 3.0 | 95.0 | 10.24 | 57.72 |
| 12 | 30.0 | 2.0 | 5.0 | 125.0 | 14.1 | 64.69 |
| 13 | 15.0 | 2.0 | 3.0 | 95.0 | 17.67 | 77.85 |
| 14 | 30.0 | 3.0 | 3.0 | 115.0 | 12.3 | 66.21 |
| 15 | 0.0 | 2.0 | 1.0 | 10.0 | 19.39 | 88.15 |

Note:
*The observed values of Y1, Y2 and Y3 represent the means of three determinations; standard deviations were <5% of the mean and thus are omitted from the table. X1; ALA in TPGS, X2; citral concentration, X3; PG concentration, Y1; elongation %, Y2; initial permeation after 2 h, Y3; cumulative permeation after 24 h.
Abbreviations:
VNP; Vinpocetine, ALA; alpha lipoic acid, TPGS; D-a-Tocopherol polyethylene glycol 1000 succinate, PG; propylene glycol concentration.

Characterization of the Prepared VNP-TPGS-ALA Transdermal Films

Physical appearance of the prepared films were investigated using magnifying glass 1E) for surface appearance and defects. Film thickness was measured using micrometer (Mitutoyo Co., Kawasaki-shi, Kanagawa-ken, Japan).

Film Elongation Percent

The prepared films were evaluated for percent elongation as previously described.[32] Briefly, Rectangular film strips of 1 cm×4 cm were fixed in such a way that the length of film between the jaws was 2 cm under weight of 200 g for a minute. The elongation % was calculated according to equation (1).

$$\text{Elongation \%} = \left(\frac{\text{Final film length} - \text{Original film length}}{\text{Original film length}}\right) \times 100 \quad \text{equation (1)}$$

Ex Vivo Diffusion Study of the Prepared VNP-TPGS-ALA Transdermal Films

The study protocol was approved by the Research Ethics Committee, Faculty of Pharmacy, King Abdulaziz University that ensured the care and use of animals according to the EU Directive 2010/63/EU on the protection of animals used for scientific purposes and Guiding Principle in Care and Use of Animals (DHEW publication NIH 80-23). Full thickness skin samples of 3×3 cm area from the abdominal region of shaved Wistar rats were excised and freed from any subcutaneous fats. The prepared skin was mounted between the donor and receptor compartments of the diffusion cells with the dermal side in direct contact with the receptor medium. The diffusion of VNP from the prepared transdermal films (15 formulations) were carried out using automated Franz diffusion cell apparatus (MICROETTEPLUSS™, Hanson Research, Chatsworth, Calif., USA) with 1.77 cm² of diffusion area.[31] Buffered saline solution (pH 7.4) was used as a receiver medium in the receptor chamber in which the temperature was kept at 37° C. and the stirring rate was 400 rpm. VNP samples were analyzed using a previously reported high-performance liquid chromatography (HPLC) method validated and adopted to our laboratory.[33]

Optimization of VNP-TPGS-ALA Micelles Loaded Transdermal Film

The results obtained for the responses ($Y_1$-$Y_3$) of the prepared 15 formulations were subjected to statistical analysis and the optimum combination of these factors was deduced. The predicted VNP-TPGS-ALA micelles loaded transdermal film, deduced by the design, utilizing the optimum level of factors was prepared and evaluated for elongation % and diffusion parameters. The observed data obtained was compared with the predicted values for validation of the optimized formulation.

Visualization of Skin Penetration for the Optimized TPGS-ALA Loaded Transdermal Film Using Fluorescence Laser Microscope FITC-dextran (permeability tracer, 0.15 μmol/mL) was used instead of VNP in the preparation of the optimized transdermal formulation.[34-36] FITC-dextran loaded micelle transdermal films were added on the rat skin and the penetration of FITC-dextran across the rat skin was investigated. Transdermal film loaded with raw FITC-dextran (control), i.e. no micelles included, was prepared and treated as described for labelled optimized transdermal formulation. The treated skin was removed after 0.5, 2 and 4 h and kept in 10% buffered formalin as a fixative.[37,38] Blocks of skin sample paraffin wax 4 μm thick sections were prepared using a microtome. The prepared samples were observed using Zeiss Axio Observer D1 Inverted Dic Fluorescence microscope (Carl Zeiss AG, Oberkochen, Germany). Filter used was 470/40 nm excitation, 495 beam splitter and 525/50 nm emission. Images were acquired with identical acquisition parameters, with minimum excitation and gain.

Results and Discussion

Preparation and Characterization of VNP-TPGS-ALA Micelles

The main factors that affect micelles ability to deliver drugs include solubilizing capacity and stability. The choice of TPGS in this study was based on its ability to form stable micelles and to efficiently solubilize poorly soluble drugs owing to its low CMC and high HLB. TPGS was also reported as a skin permeation enhancer.[39,40] LA is a powerful antioxidant that could enhance the cognitive function in case of Alzheimer's disease. ALA molecules act as surface active agent, reduce the surface energy, and spontaneously aggregate in aqueous medium to form micelles.[26] Li et al, proved ALA ability to stabilize and enhance drug loading of polymeric micelles.[41] Accordingly, incorporation of ALA could provide combined advantages of micelles stabilization and drug loading enhancement. In addition, augmenting the cognitive improving action of VNP.

Figure 1B:
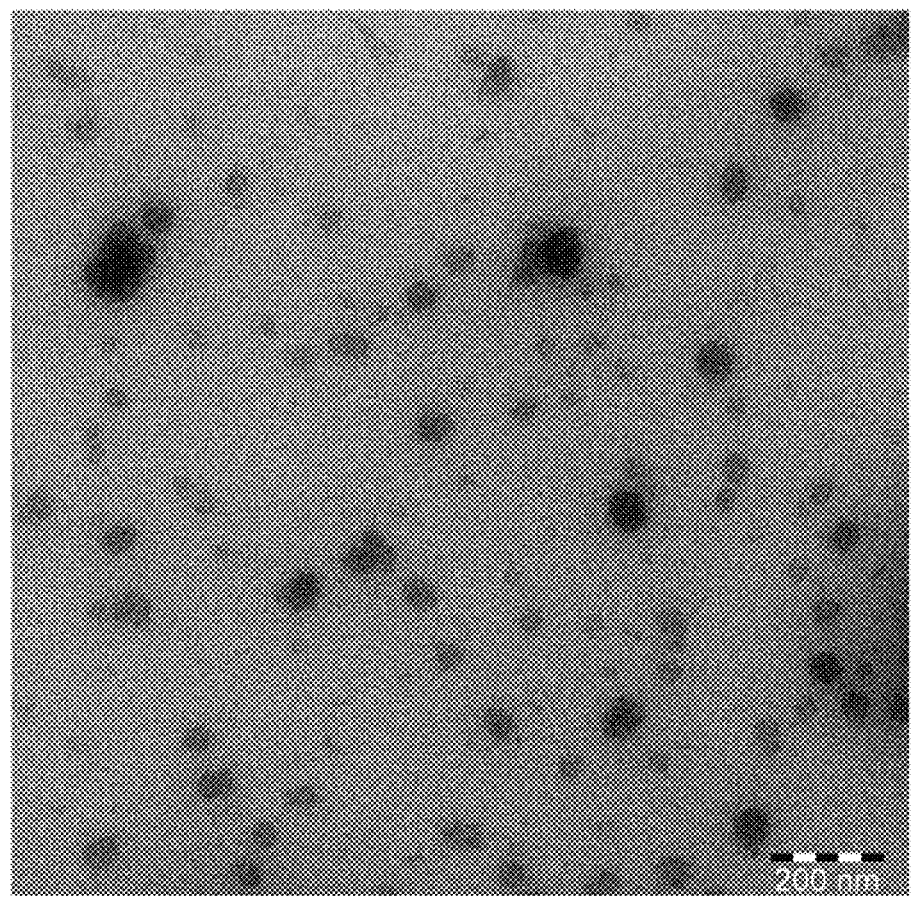

The prepared VNP-TPGS-ALA micelles showed average particle size, measured by the dynamic light scattering technique of 129±18 nm with polydispersity index of 0.59 (FIG. 1A). Photomicrographs of VNP-TPGS-ALA micelles preparation examined by TEM, shown in FIG. 1B, revealed a wide range of sizes of clusters for VNP TPGS ALA micelles with larger clumps that are interpreted as micelle aggregates.

Preparation and Characterization of VNP-TPGS-ALA Transdermal Films

The prepared transdermal films were smooth in appearance, uniform in thickness without visible cracks. The results of the elongations % ($Y_1$), the initial permeation after 2 h ($Y_2$) and the cumulative permeation after 24 h ($Y_3$) for VNP-TPGS-ALA transdermal films are presented in Table 2 and FIG. 2.

Box-Behnken Experimental Design for VNP-TPGS-ALA Transdermal Films

The quantitative effects of the independent variables ($X_1$-$X_3$) on the dependent variables ($Y_1$-$Y_3$) have been fitted into the regression quadratic equations (equations 2-4).

$$\text{Elongation \%} = -19.531 + 0.347X_1 - 27.708X_2 + 59.063X_3 + 0.012X_1^2 - 0.083X_1X_2 - 0.125X_1X_3 + 5.208X_2^2 + 4.375X_2X_3 - 6.198X_3^2 \quad \text{equation(2)}$$

$$\text{Initial permeation after 2 h} = 12.5297 - 0.089X_1 + 1.224X_2 + 3.278X_3 - 0.002X_1^2 - 0.112X_1X_2 - 0.005X_1X_3 + 1.207X_2^2 - 0.908X_2X_3 - 0.126X_3^2 \quad \text{equation (3)}$$

$$\text{Cumulative permeation after 24 h} = 70.354 - 0.750X_1 + 10.523X_2 + 2.014X_3 - 0.0004X_1^2 - 0.036X_1X_2 - 0.031X_1X_3 - 2.178X_2^2 + 1.393X_2X_3 - 0.449X_3^2 \quad \text{equation (4)}$$

Figure 3A:
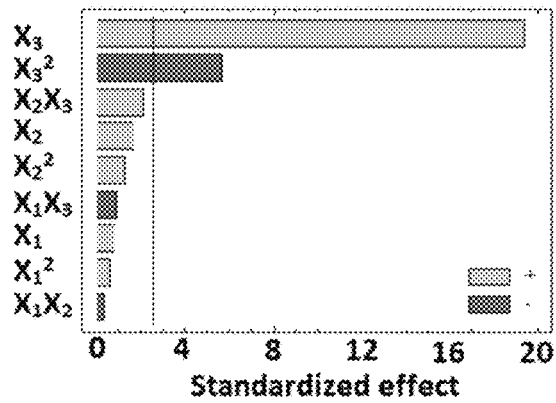
FIG. 3A-C. Standard Pareto charts revealing the significance of the independent variables (X1, X2 and X3) and their combined effects on the investigated dependent variables Y1 (A); Y2 (B); and Y3 (C). X1; ALA in TPGS, X2; citral concentration, X3; PG, Y1; elongation %, Y2; initial permeation after 2 h, Y3; cumulative permeation after 24 h.

The significance and magnitude of the effects for the investigated dependent variables on the studied responses are represented using Pareto charts and 3D response surface plots in FIG. 3 and FIG. 4, respectively. The synergistic and antagonistic effects of the independent variables are indicated by the positive and negative signs in the Pareto charts.

Estimated effects of factors and associated p-values for the dependent variables are presented in Table 3. P-value less than 0.05 is considered significant. The estimate values in Table 3 reflect the magnitude of the effect of each factor on the response relative to the other factors. The greater the absolute value of the estimate, the more the effect of that factor on the studied response. The estimate's sign designates the trend's direction. A positive sign of an estimate denotes a direct correlation of the variable with the studied response and a negative sign denotes an inverse one.

TABLE 3

Estimated effects of factors and associated p-values for dependent variables (Y1, Y2, and Y3).

| Factor | Y1 Estimated effect | Y1 p value | Y2 Estimated effect | Y2 p value | Y3 Estimated effect | Y3 p value |
|---|---|---|---|---|---|---|
| X1 | 5.0 | 0.4391 | −11.2875 | 0.0015* | −27.8025 | 0.0001* |
| X2 | 10.0 | 0.1537 | 3.3 | 0.1259 | 10.9025 | 0.0061* |
| X3 | 115.0 | 0.0000* | 2.4925 | 0.2243 | 6.565 | 0.0405* |
| $X_1^2$ | 5.41667 | 0.5634 | −0.700833 | 0.8017 | −0.175833 | 0.9621 |
| X1X2 | −2.5 | 0.7784 | −3.36 | 0.2436 | −1.075 | 0.7634 |
| X1X3 | −7.5 | 0.4137 | −0.325 | 0.9033 | −1.86 | 0.6060 |
| $X_2^2$ | 10.4167 | 0.2878 | 2.41417 | 0.4035 | −4.35583 | 0.2708 |
| X2X3 | 17.5 | 0.0921 | −3.63 | 0.2128 | 5.57 | 0.1604 |

TABLE 3-continued

Estimated effects of factors and associated p-values for dependent variables (Y1, Y2, and Y3).

| | Response | | | | | |
|---|---|---|---|---|---|---|
| | Y1 | | Y2 | | Y3 | |
| Factor | Estimated effect | p value | Estimated effect | p value | Estimated effect | p value |
| $X_3^2$ | −49.5833 | 0.0024* | −1.01083 | 0.7182 | −3.59083 | 0.3544 |
| $R^2$ | 98.8172 | | 90.8485 | | 97.1272 | |
| Adj. $R^2$ | 96.6882 | | 74.3758 | | 91.9562 | |
| SEE | 8.41625 | | 2.54266 | | 3.38154 | |
| MAE | 4.11111 | | 1.21089 | | 1.69456 | |

NOTE:
*Significant effect of factors on individual dependent variables X1; ALA in TPGS, X2; citral concentration, X3; PG, Y1; elongation %, Y2; initial permeation after 2 h, Y3; cumulative permeation after 24 h cumulative amount of VNP.
Abbreviations:
VNP; Vinpocetine, ALA; alpha lipoic acid, TPGS; D-a-Tocopherol polyethylene glycol 1000 succinate, PG; propylene glycol concentration, $R^2$; the coefficient of determination, Adj. $R^2$; the coefficient of determination, adjusted for degrees of freedom, SEE; Standard Error of Estimate., MAE; Mean absolute error.

Effect on the Elongation Percent ($Y_1$)

Generally, the elongation percent reflects the mechanical properties of the prepared transdermal film. A hard and brittle film was characterized by moderate tensile strength and low elongation but a soft and tough film is described by high tensile strength and high elongation.[42] So, the incorporation of the appropriate plasticizer concentration is important to improve the elasticity, increase toughness and reduce the brittleness of the prepared film.[43] To obtain a tough but flexible film, the current study aimed to investigate the effect of PG at different levels from 1 to 5%. The obtained results in Table 2 showed that elongation percentage varied from 5% (F4) to 140% (F9). The statistical analysis revealed that PG ($X_3$) and its quadratic term showed positive significant effects on the elongation % ($Y_1$) (FIG. 3A) with p-values of 0.0001 and 0.0024, respectively (Table 3). These results indicated that the plasticizer percentage ($X_3$) was the most significant factor affecting the elongation percent ($Y_1$). The 3D response surface graph illustrated in FIGS. 4A & B) demonstrated the magnitude of this effect. This finding could be explained because of polymer chain interruption by the action of PG that leads to softening and extending the film matrix. This finding for increasing the elongation percentage of films by the action of PG is in accordance with the previously reported data.[32,44,45]

Effect on Initial Drug Permeation After 2 h ($Y_2$)

Figure 2A:
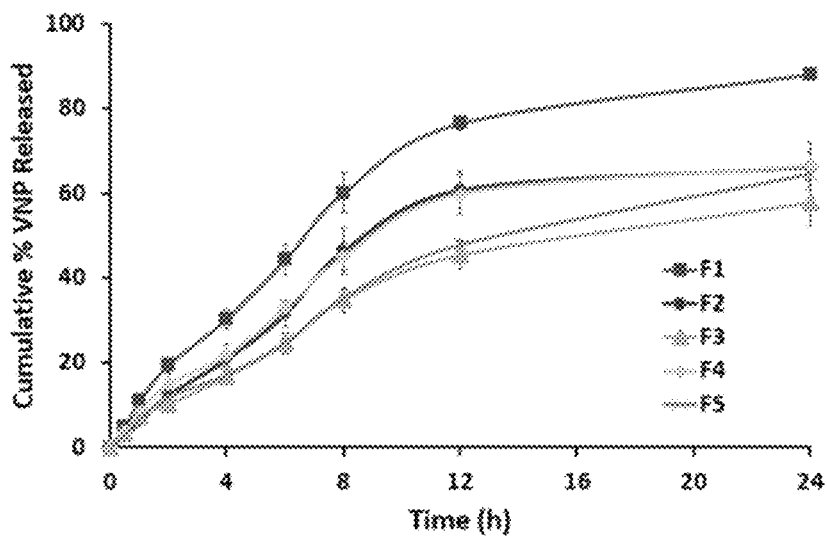
FIG. 2A-C. Ex vivo permeation profile of VNP-TPGS-ALA transdermal patch formulations: (A) F1-F5; (B) F6-F10; and (C) F11-F15.
Figure 2B:
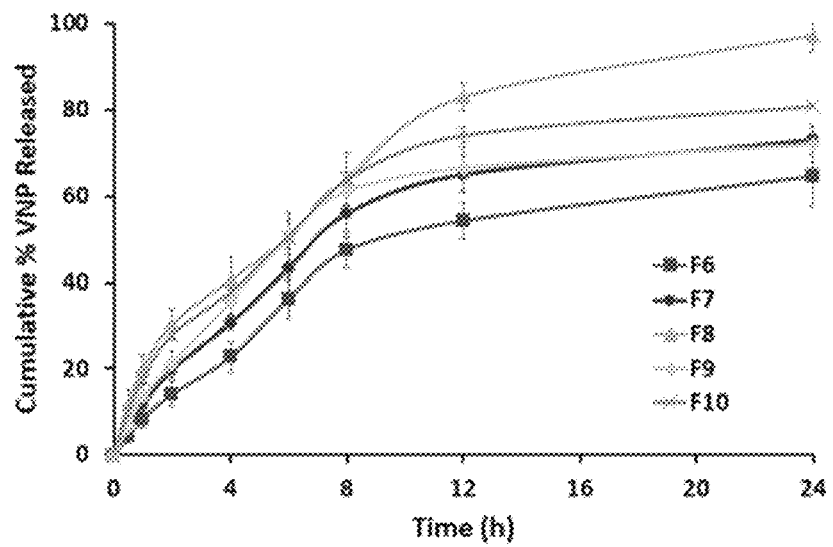
Figure 2C:
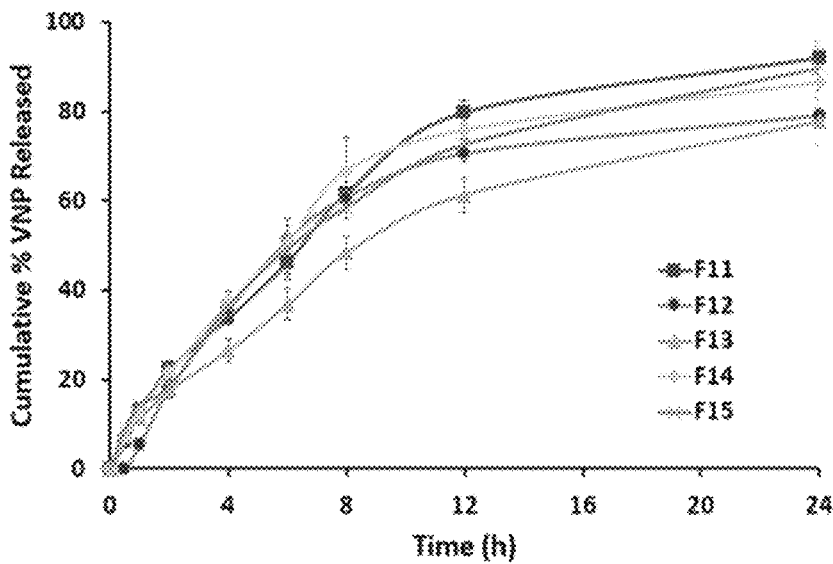
Figure 3B:
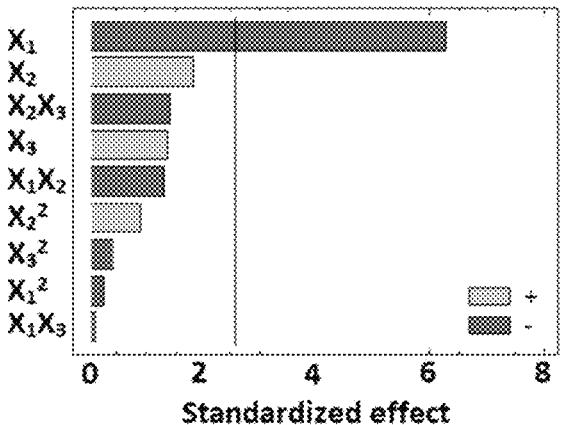
Figure 4A:
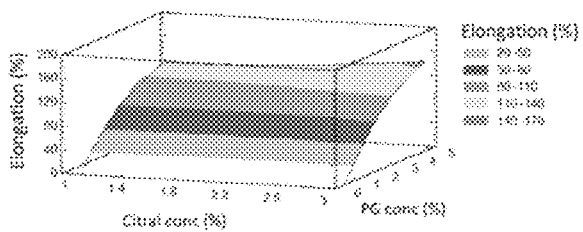
FIG. 4A-F. 3D response surface plots showing the effects of the independent variables X1 and X2 at midpoint of X3 on the investigated dependent variables Y1 (A & B); Y2 (C); and Y3 (D, E & F). X1; ALA in TPGS, X2; citral concentration, X3; PG, Y1; elongation %, Y2; initial permeation after 2 h, Y3; cumulative permeation after 24 h.
Figure 4B:
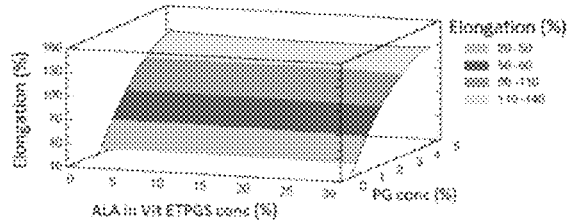
Figure 4C:
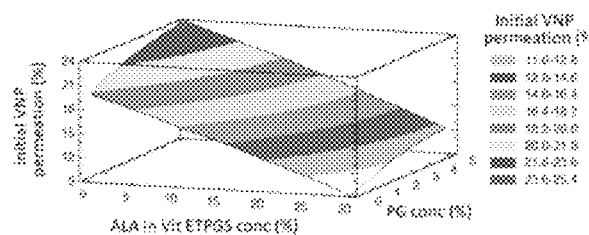

Permeation profiles of VNP-TPGS-ALA transdermal films with no ALA in their content displayed the highest initial VNP permeation after 2 h ranging from 19.39 (F15) to 30.36% (F10). Whereas, formulations containing the highest percentage of ALA (30%) displayed the lowest initial VNP permeation after 2 h ranging from 10.24 to 14.1% for F11 and F12, respectively (FIG. 2). At the same levels of $X_2$ and $X_3$, when $X_1$ increased from 0 to 30%, $Y_2$ values decreased from 21.58% (F8) to 10.24% (F11), from 19.39% (F15) to 11.84% (F6), from 30.38% (F10) to 12.3% (F14), and from 22.3% (F2) to 14.1% (F12). As illustrated in FIGS. 3B and 4C, the percentage of ALA in TPGS ($X_1$) is the only factor that significantly affected the initial permeation after 2 h ($Y_2$) in a negative trend with p-value of 0.0015 (Table 3). This finding could be attributed to the poor aqueous solubility of ALA that could result in reduced hydrophilicity of TPGS-ALA micelles, and consequently, reduced permeation rate of VNP from VNP-TPGS-ALA films.[22]

Effect on the Cumulative Drug Permeated after 24 h ($Y_3$)

Figure 3C:
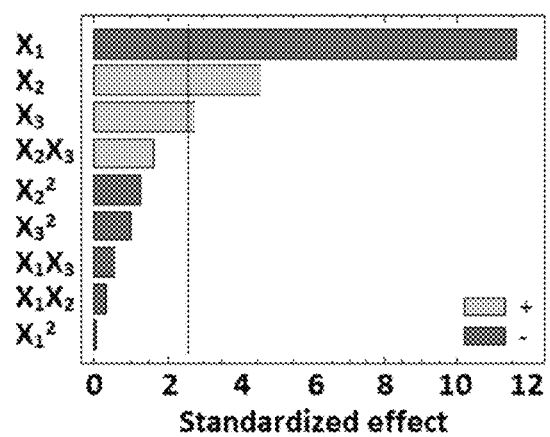
Figure 4D:
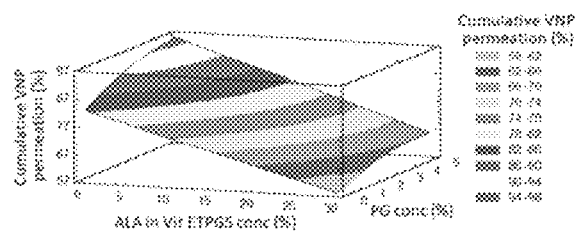
Figure 4E:
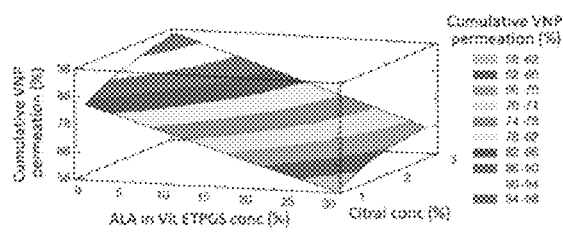
Figure 4F:
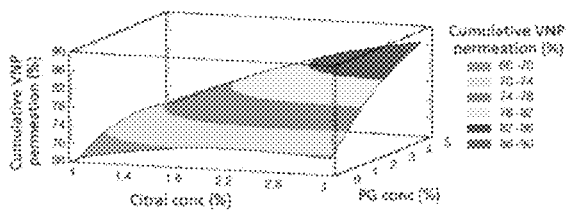

The permeation behavior of VNP from the prepared transdermal films showed a marked variation in the cumulative drug permeated after 24 h ranging from 57.72% to 97.29% according to the level of factors in the formulations as shown in FIG. 2. All the studied factors ($X_1$, $X_2$ and $X_3$) showed significant effect on the cumulative amount of VNP permeation after 24 h ($Y_3$) as illustrated in FIG. 3C. The percentage of ALA in TPGS ($X_1$) showed an antagonistic significant effect on the cumulative drug permeation after 24 h ($Y_3$) with p-value of 0.0001. On the other hand, the percentage of citral ($X_2$), and the percentage of PG ($X_3$) showed a synergistic significant effect on the same response with p-values of 0.0061, and 0.0405, respectively (Table 3). The magnitude of the effect of the three factors on $Y_3$ is illustrated in FIGS. 4D, E & F).

Incorporation of $X_1$ with high level (30%) in VNP-TPGS-ALA transdermal films led to a controlled-release pattern. At the same levels of $X_2$ and $X_3$, when the $X_1$ increased from 0 to 30%, $Y_3$ decreased from 86.65% (F8) to 57.72% (F11), from 88.15% (F15) to 64.41% (F6), from 97.29% (F10) to 66.21% (F14), and from 92.15% (F2) to 64.69% (F12). This could be due to low aqueous solubility of ALA.

On the other hand, as the percentage of citral ($X_2$, penetration enhancer) increased, the percent of VNP permeated via the rat skin increased. At the same levels of $X_1$ and $X_3$, when $X_2$ increased from 1 to 3% $Y_3$ increased from 86.65% (F8) to 97.29% (F10), from 66.43% (F3) to 73.1% (F4), and from 57.72% (F11) to 66.21% (F14). This finding could be attributed to the presence of citral in the film which may interact with some components of the skin causing increased fluidity in the intercellular lipid lamellae, and/or leach out some of the structural components, which increases the level of drug penetration through the barrier membrane.[46,47] The penetration enhancer may also reduce the capacity of drug binding to the skin, thereby improving drug transport.[43,48] A similar permeation enhancing effect of citral was reported by Ali et al., who developed glibenclamide transdermal matrix system.[49]

The same finding was found with $X_3$, as the percentage of PG ($X_3$, plasticizer) increased, the percent of VNP permeated via the rat skin increased. At the same levels of $X_1$ and $X_2$, when the $X_3$ increased from 1 to 5% $Y_3$ increased from 88.15% (F15) to 92.15% (F2), from 66.43% (F3) to 71.85% (F1), and from 64.41% (F6) to 64.69% (F12). It has been reported that the selection of a suitable plasticizer and its proper percentage has an impact not only on the mechanical properties of the film but also on its permeability of drugs.[50] So, the incorporation of PG ($X_3$) as a plasticizer increases the mobility of the chain of the film forming polymer leading to increased amount of drug release. The plasticizer will interpose itself between the polymer chains and interact with the forces held together by extending and softening the polymer matrix.[47,51] Another explanation that may enforce the obtained finding is the presence of hydroxyl groups in PG that would strongly interact with water and/or with hydroxypropyl methylcellulose via hydrogen bonding. Hence, the use of PG allowed for more water absorption by the film and thus facilitating VNP diffusion.[32,52] This result was in accordance with Namrata and Madan who observed a permeation enhancing effect of PG when used as a plasticizer in carvedilol transdermal systems.[53]

Optimization of VNP-TPGS-ALA Transdermal Films

The optimum combination of the factors were obtained by numerical optimization. The results deduced optimum VNP-TPGS-ALA transdermal film formulation of 16.62% for ALA % in TPGS, 3.0% for citral concentration and 2.18% for PG concentration. The deduced optimized VNP-TPGS-ALA transdermal film formulation was prepared and evaluated. The results of the observed and the predicted values are presented in Table 4. According to these results, the optimized VNP-TPGS-ALA transdermal film formulation independent factors combination produced the desired elongation % and controlled drug permeation.

TABLE 4

Optimal calculated variables and observed, predicted and residual values for responses

| Independent variable | Optimum | Dependent variable | Predicted | Observed | Residual |
|---|---|---|---|---|---|
| ALA in TPGS (%) | 16.62 | Elongation (%) | 72.5 | 75.69 | 3.19 |
| Citral concentration (%) | 3.0 | Initial permeation after 2 h (%) | 19.98 | 18.89 | 1.09 |
| PG concentration (%) | 2.18 | Cumulative permeation after 24 h (%) | 78.2 | 74.74 | 3.46 |

Abbreviations:
ALA; alpha lipoic acid, TPGS; D-a-Tocopherol polyethylene glycol 1000 succinate, PG; propylene glycol concentration.

Figure 5:
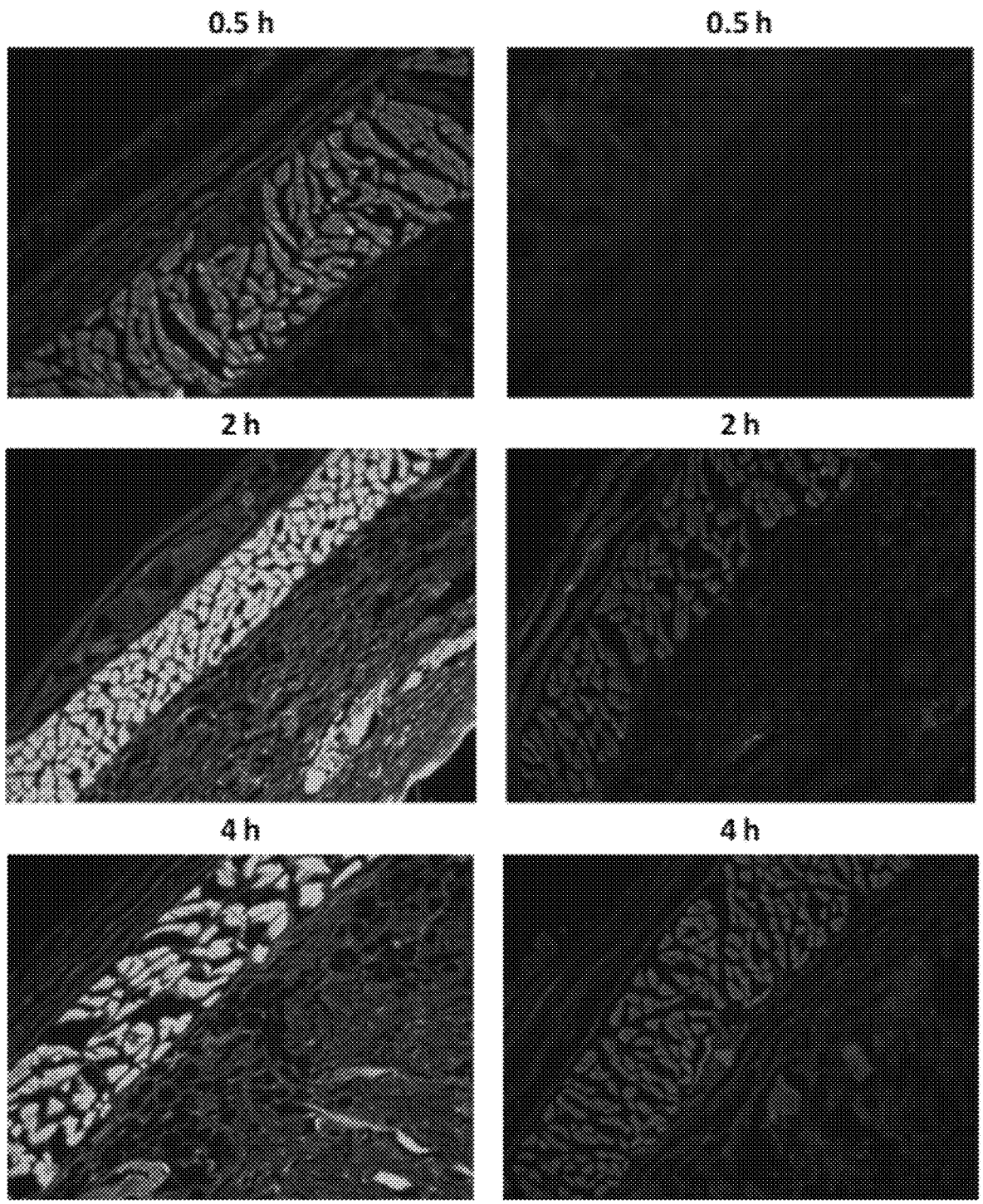
FIG. 5. Skin penetration visualization for the optimized TPGS-ALA loaded transdermal (left column) and control (right column) films after 0.5, 2 and 4 h using fluorescence laser microscope (magnification 400×).

Visualization of Skin Penetration for the Optimized VNP-TPGS-ALA Transdermal Film Using Fluorescence Laser Microscope Visualization of the permeation extent for the prepared optimized FITC-dextran loaded-TPGS-ALA transdermal film using fluorescence laser microscope was carried out in comparison with raw FITC-dextran loaded transdermal film. The images revealed marked widespread fluorescence intensity in skin tissue from FITC-dextran loaded-TPGS-ALA transdermal film formulation after 0.5, 2 and 4 h compared to raw FITC-dextran loaded transdermal formulation as shown in FIG. 5. Laser microscope results clearly revealed penetration enhancement from FITC-dextran loaded-TPGS-ALA transdermal film formulation through different skin layers. This result could be attributed to the entrapment of drug in the micellar structure of TPGS-ALA that enhances its penetration through skin layers compared with raw film. The results revealed the ability of penetration enhancement through skin tissue attained by the optimized TPGS-ALA transdermal film formulation when compared with raw transdermal formulation.

CONCLUSION

TPGS and ALA were utilized as nanostructured micellar formulation for transdermal penetration enhancement of VNP. The optimized TPGS-ALA micelles loaded transdermal film showed ability to improve permeation of VNP through skin layers compared with raw VNP loaded transdermal film. The results deduced optimum VNP-TPGS-ALA transdermal film formulation of 16.62%, 3.0% and 2.18% for $X_1$, $X_2$ and $X_3$, respectively. The marked widespread fluorescence intensity clearly revealed penetration enhancement through skin tissue attained by the optimized TPGS-ALA transdermal film formulation after 0.5, 2 and 4 h compared with raw transdermal formulation. These findings highlighted the use of VNP-TPGS-ALA micellar loaded film for enhancing the transdermal delivery of the loaded drug.

REFERENCES

1. Kidd P M. A review of nutrients and botanicals in the integrative management of cognitive dysfunction. *Altern Med Rev.* 1999; 4(3):144-161. ncbi.nlm.nih.gov/pubmed/10383479. Accessed Oct. 31, 2018.
2. Kong L, Song C, Ye L, Guo D, Yu M, Xing R. The Effect of Vinpocetine on Human Cytochrome P450 Isoenzymes by Using a Cocktail Method. Evidence-based *Complement Altern Med.* 2016. doi:10.1155/2016/5017135
3. Zhang Y, Li J, Yan C. An update on vinpocetine: New discoveries and clinical implications. *Eur J Pharmacol.* 2018; 819:30-34. doi:10.1016/j.ejphar.2017.11.041
4. Patyar S, Prakash A, Modi M, Medhi B. Role of vinpocetine in cerebrovascular diseases. *Pharmacol Rep.* 2011; 63(3):618-628. ncbi.nlm.nih.gov/pubmed/21857073. Accessed Oct. 31, 2018.
5. El-Laithy H M, Shoukry O, Mahran L G. Novel sugar esters proniosomes for transdermal delivery of vinpocetine: Preclinical and clinical studies. *Eur J Pharm Biopharm.* 2011; 77(1):43-55. doi:10.1016/J.EJPB.2010.10.011
6. Ahmed O A A, Badr-Eldin S M, Tawfik M K, Ahmed T A, El-Say K M, Badr J M. Design and optimization of self-nanoemulsifying delivery system to enhance quercetin hepatoprotective activity in paracetamol-induced hepatotoxicity. *J Pharm Sci.* 2014; 103(2):602-612. doi:10.1002/jps.23834
7. Ahmed T A, El-Say K M. Development of alginate-reinforced chitosan nanoparticles utilizing W/O nanoemulsification/internal crosslinking technique for transdermal delivery of rabeprazole. *Life Sci.* 2014; 110(1):35-43. doi:10.1016/j.lfs.2014.06.019
8. Badr-Eldin S M, Ahmed O A A. Optimized nano-transfersomal films for enhanced sildenafil citrate transdermal delivery: Ex vivo and in vivo evaluation. *Drug Des Devel Ther.* 2016; 10:1323-1333. doi:10.2147/DDDT.S103122
9. Alexander A, Dwivedi S, Ajazuddin, et al. Approaches for breaking the barriers of drug permeation through transdermal drug delivery. *J Control Release.* 2012; 164(1):26-40. doi:10.1016/j.jconrel.2012.09.017
10. Zhang Z, Tan S, Feng S S. Vitamin E TPGS as a molecular biomaterial for drug delivery. *Biomaterials.* 2012; 33(19):4889-4906. doi:10.1016/j.biomaterials.2012.03.046
11. Guo Y, Luo J, Tan S, Otieno B O, Zhang Z. The applications of Vitamin E TPGS in drug delivery. *Eur J Pharm Sci.* 2013; 49(2):175-186. doi:10.1016/J.EJPS.2013.02.006

12. Raju A, Muthu M S, Feng S-S. Trastuzumab-conjugated vitamin E TPGS liposomes for sustained and targeted delivery of docetaxel. *Expert Opin Drug Deliv.* 2013; 10(6):747-760. doi:10.1517/17425247.2013.777425
13. Mi Y, Zhao J, Feng S-S. Vitamin E TPGS prodrug micelles for hydrophilic drug delivery with neuroprotective effects. *Int J Pharm.* 2012; 438(1-2):98-106. doi:10.1016/j.ijpharm.2012.08.038
14. Zhao J, Mi Y, Feng S-S. Targeted co-delivery of docetaxel and siPlk1 by herceptin-conjugated vitamin E TPGS based immunomicelles. *Biomaterials.* 2013; 34(13):3411-3421. doi:10.1016/j.biomaterials.2013.01.009
15. Wang G, Yu B, Wu Y, Huang B, Yuan Y, Liu C S. Controlled preparation and antitumor efficacy of vitamin E TPGS-functionalized PLGA nanoparticles for delivery of paclitaxel. *Int J Pharm.* 2013; 446(1-2):24-33. doi:10.1016/j.ijpharm.2013.02.004
16. Packer L, Witt E H, Tritschler H J. Alpha-lipoic acid as a biological antioxidant. *Free Radic Biol Med.* 1995; 19(2):227-250. doi:10.1016/0891-5849(95)00017-R
17. Alan C, Kocoglu H, Resit Ersay A, Anil Kurt H, Ertung Y, Alan H. [Biochemical changes in cavernosal tissue caused by single sided cavernosal nerve resection and the effects of alpha lipoic acid on these changes]. *Actas Urol Esp.* 2010; 34(10):874-881. doi:13184376 [pii]
18. Keegan A, Cotter M A, Cameron N E. Effects of diabetes and treatment with the antioxidant α-lipoic acid on endothelial and neurogenic responses of corpus cavernosum in rats. *Diabetologia.* 1999; 42(3):343-350. doi:10.1007/s001250051161
19. Nahar P, Shah S, Kshirsagar M, Ghongane B, Udupa A. A comparative study of effects of omega-3 fatty acids, alpha lipoic acid and vitamin E in type 2 diabetes mellitus. *Ann Med Health Sci Res.* 2013; 3(3):442. doi:10.4103/2141-9248.117954
20. Mitkov M D, Aleksandrova I Y, Orbetzova M M. Effect of transdermal testosterone or alpha-lipoic acid on erectile dysfunction and quality of life in patients with type 2 diabetes mellitus. *Folia Med (Plovdiv).* 2013; 55(1):55-63. degruyter.com/view/j/folmed.2013.55.issue-1/folmed.2013.55.issue-1/folme-2013-0006/folmed-2013-0006.xml. Accessed Mar. 15, 2018.
21. Bustamante J, Lodge J K, Marcocci L, Tritschler H J, Packer L, Rihn B H. α-lipoic acid in liver metabolism and disease. *Free Radic Biol Med.* 1998; 24(6):1023-1039. doi:10.1016/S0891-5849(97)00371-7
22. Ziegler D, Nowak H, Kempler P, Vargha P, Low P A. Treatment of symptomatic diabetic polyneuropathy with the antioxidant α-lipoic acid: A meta-analysis. *Diabet Med.* 2004; 21(2):114-121. doi:10.1111/j.1464-5491.2004.01109.x
23. Shinto L, Quinn J, Montine T, et al. A Randomized Placebo-Controlled Pilot Trial of Omega-3 Fatty Acids and Alpha Lipoic Acid in Alzheimer's Disease. *J Alzheimer's Dis.* 2013; 38(1):111-120. doi:10.3233/JAD-130722
24. Fava A, Pirritano D, Plastino M, et al. The Effect of Lipoic Acid Therapy on Cognitive Functioning in Patients with Alzheimer's Disease. *J Neurodegener Dis.* 2013; 2013:454253. doi:10.1155/2013/454253
25. Kofuji K, Nakamura M, Isobe T, Murata Y, Kawashima S. Stabilization of α-lipoic acid by complex formation with chitosan. *Food Chem.* 2008; 109(1):167-171. doi:10.1016/j.foodchem.2007.11.078
26. Nishiura H, Sugimoto K, Akiyama K, et al. A Novel Nano-Capsule of α-Lipoic Acid as a Template of Core-Shell Structure Constructed by Self-Assembly. *J Nanomed Nanotechnol.* 2013; 04(01):1-7. doi:10.4172/2157-7439.1000155
27. Ahmed O A A. Development and single dose clinical pharmacokinetics investigation of novel zein assisted-alpha lipoic acid nanoencapsulation of vardenafil. *Sci Rep.* 2018; 8(1):15802. doi:10.1038/s41598-018-34235-8
28. Abourehab M A S, Ahmed O A A, Balata G F, Almalki W H. Self-assembled biodegradable polymeric micelles to improve dapoxetine delivery across the blood-brain barrier. *Int J Nanomedicine.* 2018; 13:3679-3687. doi:10.2147/IJN.S168148
29. Ahmed O A A, Badr-Eldin S M. In situ misemgel as a multifunctional dual-absorption platform for nasal delivery of raloxifene hydrochloride: formulation, characterization, and in vivo performance *Int J Nanomedicine.* 2018; Volume 13:6325-6335. doi:10.2147/IJN.S181587
30. El-Say K M, El-Helw A., Ahmed O A A, et al. Statistical optimization of controlled release microspheres containing cetirizine hydrochloride as a model for water soluble drugs. *Pharm Dev Technol.* 2015; 20(6). doi:10.3109/10837450.2014.920353
31. Ahmed O A A, Afouna M I, El-Say K M, Abdel-Naim A B, Khedr A, Banjar Z M. Optimization of self-nanoemulsifying systems for the enhancement of in vivo hypoglycemic efficacy of glimepiride transdermal patches. *Expert Opin Drug Deliv.* 2014; 11(7). doi:10.1517/17425247.2014.906402
32. El-Say K M K M, Ahmed O A A A O A A, Aljaeid B M B M, Zidan A S A S. Matrix-type transdermal films to enhance simvastatin ex vivo skin permeability. *Pharm Dev Technol.* 2017; 22(4). doi:10.3109/10837450.2015.1102279
33. Elkady E F, Tammam M H, Mohamed A A. Development and Validation of an RP-HPLC Method for the Determination of Vinpocetine and Folic Acid in the Presence of a Vinpocetine Alkaline Degradation Product in Bulk and in Capsule Form. *J AOAC Int.* 2017; 100(3):671-676. doi:10.5740/jaoacint.16-0239
34. Ahmed O A, Rizg W Y. Finasteride nano-transferosomal gel formula for management of androgenetic alopecia: ex vivo investigational approach. *Drug Des Devel Ther.* 2018; Volume 12:2259-2265. doi:10.2147/DDDT.S171888
35. Hulström D, Svensjo E. Intravital and electron microscopic study of bradykinin-induced vascular permeability changes using FITC-dextran as a tracer. *J Pathol.* 1979; 129(3):125-133. doi:10.1002/path.1711290304
36. Yeon J H, Na D, Choi K, Ryu S-W, Choi C, Park J-K. Reliable permeability assay system in a microfluidic device mimicking cerebral vasculatures. *Biomed Microdevices.* 2012; 14(6):1141-1148. doi:10.1007/s10544-012-9680-5
37. Thavarajah R, Mudimbaimannar V K, Elizabeth J, Rao U K, Ranganathan K. Chemical and physical basics of routine formaldehyde fixation. *J Oral Maxillofac Pathol.* 2012; 16(3):400-405. doi:10.4103/0973-029X.102496
38. PrentØ P, Lyon H. Commercial formalin substitutes for histopathology. *Biotech Histochem.* 1997; 72(5)273-282. ncbi.nlm.nih.gov/pubmed/9408588. Accessed Oct. 31, 2018.
39. Meng X, Liu J, Yu X, Li J, Lu X, Shen T. Pluronic F127 and D-α-Tocopheryl Polyethylene Glycol Succinate (TPGS) Mixed Micelles for Targeting Drug Delivery across The Blood Brain Barrier. *Sci Rep.* 2017; 7(1):2964. doi:10.1038/s41598-017-03123-y 40. Yang C, Wu T, Qi Y, Zhang Z. Recent Advances in the Application of Vitamin E TPGS for Drug Delivery. *Theranostics.* 2018; 8(2):464-485. doi:10.7150/thno.22711
41. Li W, Peng J, Yang Q, et al. α-Lipoic acid stabilized DTX/IR780 micelles for photoacoustic/fluorescence imaging guided photothermal therapy/chemotherapy of breast cancer. *Biomater Sci.* 2018; 6(5):1201-1216. doi:10.1039/C8BM00096D
42. Lin S-Y, Lee C-J, Lin Y-Y. Drug-polymer interaction affecting the mechanical properties, adhesion strength and release kinetics of piroxicam-loaded Eudragit E films plasticized with different plasticizers. *J Control Release.* 1995; 33(3):375-381. doi:10.1016/0168-3659(94)00109-8
43. Cho C-W, Choi J-S, Kim S-J, Shin S-C Enhanced transdermal delivery of loratadine from the EVA matrix. *Drug Deliv.* 2009; 16(4):230-235. doi:10.1080/10717540902872264
44. Ahmed T A, El-Say K M. Transdermal film-loaded finasteride microplates to enhance drug skin permeation: Two-step optimization study. *Eur J Pharm Sci.* 2016; 88:246-256. doi:10.1016/j.ejps.2016.03.015
45. Nesseem D I, Eid S F, El-Houseny S S. Development of novel transdermal self-adhesive films for tenoxicam, an anti-inflammatory drug. *Life Sci.* 2011; 89(13-14):430-438. doi:10.1016/j.lfs.2011.06.026
46. Magnusson B M, Runn P. Effect of penetration enhancers on the permeation of the thyrotropin releasing hormone analogue pGlu-3-methyl-His-Pro amide through human epidermis. *Int J Pharm.* 1999; 178(2):149-159. doi:10.1016/50378-5173(98)00316-0
47. Carelli V, Di Colo G, Nannipieri E, Serafini M F. Bile acids as enhancers of steroid penetration through excised hairless mouse skin. *Int J Pharm.* 1993; 89(2):81-89. doi:10.1016/0378-5173(93)90108-R
48. El-Say K M, Ahmed T A, Badr-Eldin S M, Fahmy U A, Aldawsari H, Ahmed O A A. Enhanced permeation parameters of optimized nanostructured simvastatin transdermal films: Ex Vivo and In Vivo evaluation. *Pharm Dev Technol.* 2015; 20(8):919-926. doi:10.3109/10837450.2014.938859
49. Ali A, Trehan A, Ullah Z, Aqil M, Sultana Y. Matrix type transdermal therapeutic systems of glibenclamide: Formulation, ex vivo and in vivo characterization. *Drug Discov Ther.* 2011; 5(1):53-59.
50. Crawford R R, Esmerian O K. Effect of plasticizers on some physical properties of cellulose acetate phthalate films. *J Pharm Sci.* 1971; 60(2):312-314. doi:10.1002/jps.2600600238
51. Qussi B, Suess W G. The influence of different plasticizers and polymers on the mechanical and thermal properties, porosity and drug permeability of free shellac films. *Drug Dev Ind Pharm.* 2006; 32(4):403-412. doi:10.1080/03639040600559099
52. Mali S, Sakanaka L S, Yamashita F, Grossmann M V E. Water sorption and mechanical properties of cassava starch films and their relation to plasticizing effect. *Carbohydr Polym.* 2005; 60:283-289. doi:10.1016/j.carbpol.2005.01.003
53. Vora N, Lin S, Madan P L. Development and in-vitro evaluation of an optimized carvedilol transdermal therapeutic system using experimental design approach. *Asian J Pharm Sci.* 2013; 8(1):28-38. doi:10.1016/J.AJPS.2013.07.004

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A micelle formulation, comprising
a tocopherol;
alpha lipoic acid (ALA); and
vinpocetine.

2. The micelle formulation of claim 1, wherein the tocopherol is D-α-Tocopherol polyethylene glycol 1000 succinate (TPGS).

3. A film for transdermal drug delivery comprising micelles according to claim 1 and further comprising citral and propylene glycol.

4. The film of claim 3, wherein the percentage of ALA in tocopherol is 1-30%, the citral concentration is 1-3%, and the propylene glycol concentration is 1-5%.

5. The film of claim 4, wherein the percentage of ALA in tocopherol is 16.62%, the citral concentration is 3%, and the propylene glycol concentration is 2.18%.

6. A method of treating a cognitive disorder in a subject in need thereof, wherein the cognitive disorder is selected from the group consisting of dementia, Huntington's disease, Parkinson's disease, and Alzheimer's disease, comprising topically applying the film of claim 3 to the subject.

7. A method of treating a cerebrovascular disorder in a subject in need thereof, wherein the cerebrovascular disorder is selected from the group consisting of stroke, vertebral stenosis, intracranial stenosis, and aneurysm, comprising topically applying the film of claim 3 to the subject.

\* \* \* \* \*